(12) United States Patent
Linemann et al.

(10) Patent No.: US 7,435,856 B2
(45) Date of Patent: Oct. 14, 2008

(54) METHOD OF PREPARING DIMETHYLCETENE AND, SUBSEQUENTLY, POLYDIMETHYLCETENE FROM ISOBUTYRIC ANHYDRIDE

(75) Inventors: Reinhard Linemann, Nassandres (FR); Serge Hub, Villeurbanne (FR); Guillaume Le, Colombelles (FR); Georges Martino-Gauchi, Lyons (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 10/545,977

(22) PCT Filed: Feb. 20, 2004

(86) PCT No.: PCT/FR2004/000399

§ 371 (c)(1),
(2), (4) Date: Aug. 18, 2005

(87) PCT Pub. No.: WO2004/076508

PCT Pub. Date: Sep. 10, 2004

(65) Prior Publication Data

US 2006/0270878 A1    Nov. 30, 2006

(30) Foreign Application Priority Data

Feb. 21, 2003  (FR)  .................. 03 02219

(51) Int. Cl.
*C07C 45/87*  (2006.01)
(52) U.S. Cl. .................................. 568/301
(58) Field of Classification Search .............. 568/301
See application file for complete search history.

(56) References Cited

U.S. PATENT DOCUMENTS

| 3,201,474 A | 8/1965 | Hasek et al. | 260/585.5 |
| 5,169,994 A | 12/1992 | Sumner et al. | 568/839 |
| 5,258,556 A | 11/1993 | Sumner et al. | 568/839 |

OTHER PUBLICATIONS

Pregaglia G; Binaghi: "Polymerisation of dimethylketene. A. Dimethylketene by pyrolysis of isobutryic anhydride" Macromolecular Syntheses, vol. 1968, No. 3, 1969, pp. 152-160, XP0009016143.

*Primary Examiner*—Sikarl A Witherspoon
(74) *Attorney, Agent, or Firm*—Steven D. Boyd

(57) ABSTRACT

The present invention relates to a process for the preparation of dimethylketene (DMK) and then of polydimethylketene (PDMK) by polymerization of DMK. More specifically, the DMK is obtained by pyrolysis by isobutyric anhydride (IBAN), the latter decomposing under the effect of heat (pyrolysis) to give isobutyric acid (IBA) and DMK. One mole of pyrolyzed IBAN gives one mole of IBA and one mole of DMK.

20 Claims, 1 Drawing Sheet

1) 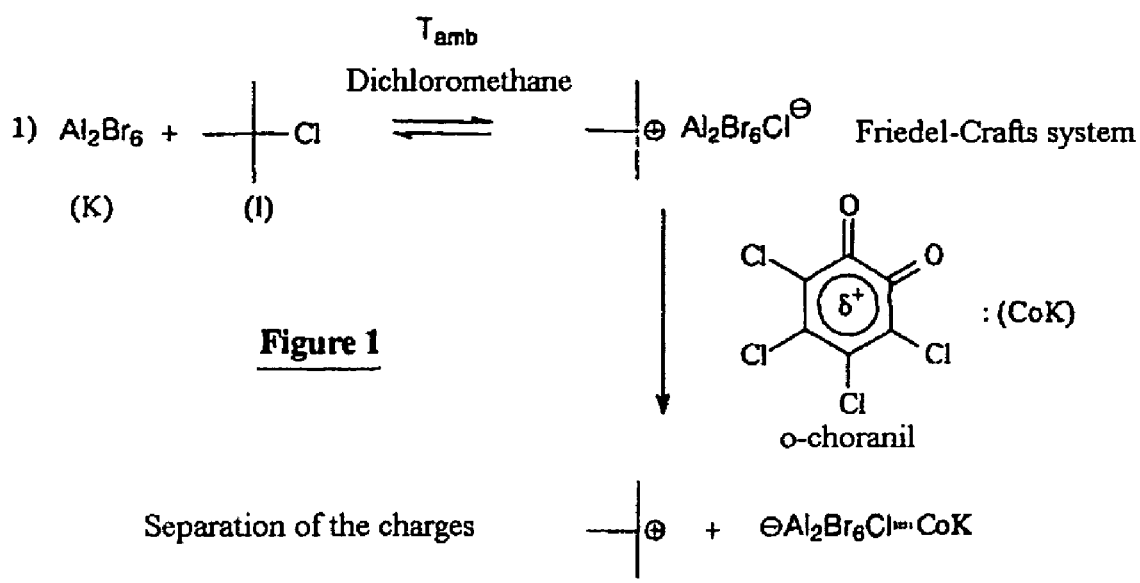
Figure 1
2) Initiation:
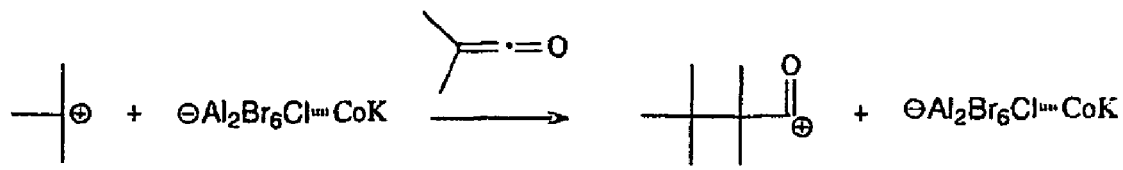

METHOD OF PREPARING DIMETHYLCETENE AND, SUBSEQUENTLY, POLYDIMETHYLCETENE FROM ISOBUTYRIC ANHYDRIDE

FIELD OF THE INVENTION

The present invention relates to a process for the preparation of dimethylketene (abbreviated to DMK in the continuation of the text) and then of polydimethylketene (abbreviated to PDMK in the continuation of the text) by polymerization of DMK. More specifically, the DMK is obtained by pyrolysis by isobutyric anhydride (abbreviated to IBAN in the continuation of the text), the latter decomposing under the effect of heat (pyrolysis) to give isobutyric acid (abbreviated to IBA in the continuation of the text) and DMK. One mole of pyrolyzed IBAN gives one mole of IBA and one mole of DMK.

BACKGROUND OF THE INVENTION

PDMK is a barrier to gases and in particular to oxygen and furthermore possesses barrier properties to moisture. It is of use in the manufacture of monolayer structures or of multilayer structures comprising a layer of PDMK and at least one layer of another material. These structures are of use in the manufacture in particular of food packagings which have to be sterilized or pasteurized.

U.S. Pat. No. 5,169,994 discloses a process for the manufacture of 2,2,4,4-tetramethylcyclobutane-1,3-diol comprising the stages consisting:

(1) in introducing IBAN into a pyrolysis region, in which the IBAN is heated to a temperature of 350 to 600° C., in order to produce an exiting vapor stream comprising DMK, IBA and unreacted IBAN;

(2) in rapidly cooling the exiting vapor stream, in order to condense the IBA and the IBAN and to separate the condensate from the DMK vapor;

(3) in introducing the DMK vapor into an absorption region, in which the DMK vapor is brought into contact with and dissolved in a solvent comprising an ester comprising from 4 to 40 carbon atoms and composed of the reaction product of an aliphatic carboxylic acid and of an alcohol, in order to produce an exiting stream comprising a solution of DMK in the solvent;

(4) in introducing the exiting stream from the absorption region into a dimerization region, in which the effluent is heated to a temperature of 70 to 140° C., in order to convert the DMK to 2,2,4,4-tetramethylcyclobutane-1,3-dione, in order to produce an exiting stream comprising a solution of 2,2,4,4-tetramethylcyclobutane-1,3-dione in the solvent; and (5) in introducing the exiting stream from the dimerization region into a hydrogenation region, in which the exiting stream is brought into contact with a hydrogenation catalyst under hydrogenation pressure and temperature conditions, in order to produce an exiting stream comprising a solution of 2,2,4,4-tetramethylcyclobutane-1,3-diol in the solvent.

In the description, it is specified that the pyrolysis stage is fed with IBAN generally as a mixture with an inert gas and under a reduced pressure, such as 20 to 500 torr. It is not known whether the reduced pressure relates to the IBAN, because of the presence of inert gas, or whether it is the mixture of IBAN and of inert gas which is under reduced pressure. In example 1, the pyrolysis of the IBAN is carried out at 250 torr and the gas recovered, after separation of the IBA and IBAN, is composed of 97% of DMK. Thus, there was no diluting gas. The degree of conversion of the IBAN in the pyrolysis, that is to say the ratio of the amount of IBAN pyrolyzed to the amount of IBAN entering the pyrolysis region, is 60%.

U.S. Pat. No. 5,258,256 discloses a process which is very similar to the preceding process but the conditions for the pyrolysis of the IBAN, with regard to the presence of inert gas, are no clearer. It is only shown in the examples that the pressure of the pyrolysis is 87, 105 or 123 torr.

SUMMARY OF THE INVENTION

It has now been found that, by carrying out the pyrolysis in the presence of an inert gas at atmospheric pressure and thus under simple operating conditions, a degree of conversion of the IBAN of at least 80%, usually between 80 and 95% (depending on the reaction conditions), is obtained.

The outlet stream from the pyrolysis is composed of DMK, of inert gas, of IBA and/or of unreacted IBAN. This stream is cooled, in order to separate the DMK and the inert gas from the IBA and/or IBAN. A stream of DMK and of inert gas still comprising a small amount of IBA is obtained. In the processes of the prior art cited above, this stream of DMK is absorbed in a solvent of ester type and then this stream of solvent, comprising the DMK, is introduced into a dimerization region. It has now been found that the stream of DMK still comprising a small amount of IBA, obtained by cooling the stream exiting from the pyrolysis, can be washed, in order to free the DMK from any trace of IBA. It is thus possible to obtain the DMK with a purity such that it can subsequently be polymerized to PDMK.

BRIEF DESCRIPTION OF THE DRAWINGS

FIG.1. is a schematic of a reaction sequence with the present invention

DETAILED DESCRIPTION OF THE INVENTION

The present invention relates to a process for the preparation of dimethylketene (DMK) by pyrolysis of isobutyric anhydride (IBAN), in which:

a) a mixture comprising 1 to 50% by volume of IBAN for respectively 99 to 50% of inert gas is preheated at atmospheric pressure between 300 and 340° C., b) this mixture is then brought to a temperature of between 400 and 550° C. for a contact time of between 0.05 and 10 s, in order to obtain a mixture of DMK, of inert gas, of isobutyric acid (IBA) and indeed even of unreacted IBAN, c) the mixture resulting from b) is cooled (stage of condensation of said mixture), in order to separate the gas mixture comprising the DMK from the condensed IBA and/or condensed IBAN.

As regards the pyrolysis of the IBAN, use may be made of any device which makes it possible to mix IBAN and an inert gas and then to bring the mixture to the required temperatures. These devices are known per se. The term "inert gas" means any gas which is not detrimentally affected during the pyrolysis of the IBAN. Mention may be made, by way of examples, of nitrogen and helium.

With regard to the proportions of IBAN and of inert gas, they are advantageously from 5 to 50% by volume of IBAN for respectively 95 to 50% of inert gas and preferably from 8 to 21% by volume of IBAN for respectively 92 to 79% of inert gas.

With regard to the contact time, it is advantageously between 0.15 and 0.25 s. A degree of conversion of the IBAN, that is to say the ratio of the amount of IBAN pyrolyzed to the amount of IBAN entering the pyrolysis region, of the order of 80 to 95% is generally obtained. The selectivity of the pyrolysis, that is to say the (number of moles of DMK obtained)/(number of moles of IBAN pyrolyzed) ratio, is of the order of 100%.

With regard to stage c), use may be made of any device which makes it possible to cool gases and to separate a gas phase from a liquid phase. These devices are known per se. It is recommended to cool the system as quickly as possible in order to avoid, at least limit, the recombination of the DMK with the IBA, which restores the IBAN.

The gas mixture comprising the DMK (inert gas essentially conveying gaseous DMK) resulting from stage c) may still comprise small proportions of IBA and/or of IBAN. According to thus an advantageous form of the invention, this gas mixture is brought into contact with a washing solution, in order to purify the DMK by reducing, indeed even by removing, any trace of IBA and/or IBAN. The gas mixture comprising the DMK resulting from stage c) is advantageously washed in a washing column filled with structured packings, said column advantageously being equipped with a demister (commercially available) positioned either at the column top or at the column bottom. Preferably, the demister is situated at the column top. The demister makes it possible, if appropriate, to stop the minute droplets (type of mist) present in the gaseous stream of DMK entering the washing column at a temperature lying in the vicinity of 10 to 50° C. and which would interfere with the purification of the DMK. This gas mixture enters at the bottom of the washing column, whereas the washing solvent enters at the column top.

Advantageously, use is made of a plate column or of a column comprising a packing. The dimensions are readily determined by a person skilled in the art depending on the properties of the gases and of the washing solution.

The washing solution can be IBAN or a saturated or unsaturated, aliphatic or alicyclic and substituted or unsubstituted hydrocarbon, the list of which is given later in the text under the heading "polymerization solvent". In the case of the use of the polymerization solvent, the DMK dissolved during this polymerization stage is stripped from the liquid phase by an inert gas stream at the column bottom. A person skilled in the art determines the pressure and temperature conditions in order for the washing solution to preferentially absorb the IBA and for a stream of DMK and of inert gas comprising as little as possible of IBA, indeed even no longer comprising any, to be obtained. If the washing solution has also absorbed DMK, it can also be passed into a low-pressure stripping column, in order to recover the DMK without stripping the IBA. IBAN is advantageously used as washing solvent.

On conclusion of the washing stage, DMK is obtained with a purity sufficient to polymerize it. The term "purity sufficient to polymerize it" is generally understood to mean a DMK having a content of IBA of less than or equal to 2000 ppm, it being known that, the less IBA, the less catalyst will subsequently be consumed in the polymerization.

The gaseous DMK (entrained by the inert carrier gas) is virtually, indeed even completely, freed from any trace of IBA and/or of IBAN, the washing solution having largely entrained the residual IBA and/or residual IBAN. On conclusion of this washing stage, a DMK with a purity of greater than 98 mol %, advantageously of greater than 99 mol %, with traces of IBA$\leq$0.2 mol % and traces of IBAN$\leq$1 mol %, advantageously$\leq$0.5 mol %, is obtained.

According to another form of the invention:
d) the gas mixture comprising the DMK prepared above is absorbed in a solvent of saturated or unsaturated, aliphatic or alicyclic and substituted or unsubstituted hydrocarbon type,
e) the DMK is then polymerized, in this solvent comprising the DMK, to PDMK in the presence of a cationic initiating system comprising an initiator (I), a coinitiator (K) and a complexing agent (CoK),
f) at the end of the reaction, the unreacted DMK is removed and the PDMK is separated from the solvent and from the residues of the initiating system.

The presence of two adjacent carbon-carbon and carbon-oxygen double bonds confers a very high reactivity on dimethylketene. It is advantageous to selectively direct the opening of one or other of the double bonds in order to promote uniform polymerization of the monomer units (A), resulting in polymers with β-ketone structure (PolyA), or uniform polymerization of the monomer units (B), resulting in polymers with structures of poly(vinyl acetal) type (PolyB), indeed even the alternating addition of the (A) and (B) units, resulting in a poly(vinyl ester) (PolyAB).

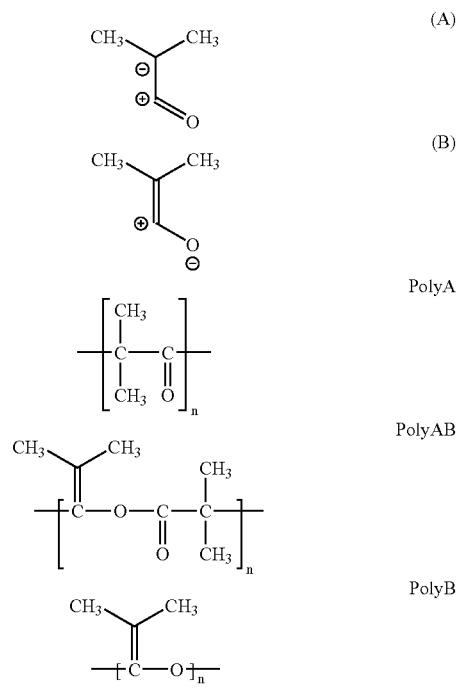

These operating conditions for the polymerization of DMK make it possible to selectively direct the polymerization toward the formation of a polymer with a β-ketone structure with very good yields, >65%, and in the presence of conventional inexpensive solvents.

Furthermore, for better efficiency and better reproducibility, homogeneous cationic initiation is prefered. This process does not result in the formation of peroxides and makes possible safe production of PDMK. Furthermore, the transfer reactions, which conventionally result in the formation of chains of low molecular mass and relatively low yields, are not observed to have a limiting effect. These various parameters make possible large scale synthesis of PDMK.

As regards the polymerization solvent, it is of saturated or unsaturated, aliphatic or alicyclic and substituted or unsubstituted hydrocarbon type. The solvents used are the conventional solvents for cationic polymerization known to a person skilled in the art. Mention may be made, by way of examples, of hydrocarbons, such as hexanes, heptanes, toluene, methylcyclohexane, ethylcyclohexane or propylcyclohexane, alkyl chlorides (primary and secondary halogenated), such as methylene chloride, ethyl chloride, propyl chloride, butyl chloride, pentyl chloride, hexyl chloride, chlorobenzene, dichlorobenzene, chloroform and the same compounds with one or more bromine atoms (according to circumstances) in place of the chlorine atom or atoms, or nonaromatic nitrated hydrocarbons, such as nitromethane, nitroethane and nitropropane. However, nontoxic and nonpolluting solvents will generally be preferred.

As regards the absorption of the DMK by the polymerization solvent, use may be made of any device for bringing a gas and a liquid into contact. Use is advantageously made of a plate column or of a column comprising a packing. The dimensions can be readily determined by a person skilled in the art according to the properties of the gases and of the solvent. A person skilled in the art can readily determine the pressure and temperature conditions in order to absorb the DMK having a purity sufficient to polymerize it and not the inert carrier gas of the gas mixture.

The solvent in which the polymerization takes place has an important role. It should not only promote the separation of the charges but also solvate the growing chains in order to slow down the precipitation while not interfering with the approach of the monomer by the formation of a solvent cage. While polar solvents promote the dissociation of the ion pairs by their high dielectric constant, and thus increase the proportion of reactive free ions, they also preferentially solvate the active centers and thus restrict the conversions by interfering with the approach of the monomer. Generally, it is not necessary for there to be obstacles to the solvation of the active centers by the DMK. In a nonpolar or moderately polar solvent, the DMK will preferably solvate the growing chains but the transfer reactions will be promoted by the solvent; the use of a complexing agent then makes it possible to limit these reactions in order to obtain high molar masses.

The solvent can, after separation from the PDMK, be reused to absorb DMK, either batchwise or by going around in a loop in a continuous process.

The catalytic system can be introduced before or after the absorption of the DMK in the solvent.

As regards the cationic initiating system, it comprises an initiator (I), a coinitiator (K) and a complexing agent (CoK).

According to one embodiment, the initiating system is chararacterized in that the complexing agent (CoK) is an agent which releases the polymerization active center from its counteranion generated by the reaction between the coinitiator (K) and the initiator (I).

According to one embodiment, the complexing agent (CoK) is a molecule having at least one double bond depleted in electrons by an electron-withdrawing group.

According to one embodiment, the coinitiator (K) is a Lewis acid of general formula $R_nMX_{3-n}$ for M an element belonging to Group IIIA, of general formula $MX_4$ for M an element belonging to Groups VA, IVA and IVB and of general formula $MX_5$ for M an element belonging to Group VB, with:

R a monovalent radical taken from the group consisting of the hydrocarbon groups of 1 to 12 carbon atoms of alkyl, aryl, arylalkyl, alkylaryl or cycloalkyl type and alkoxys;

X a halogen atom taken from the group consisting of F, Cl, Br and I;

n an integer from 0 to 3.

The phase of initiation of the cationic polymerization with $AlBr_3$ as coinitiator (K), tert-butyl chloride as initiator (I) and o-chloranil as complexing agent (CoK) is represented in FIG. 1.

The advantages of the initiating system are as follows:

the catalytic system thus generated, either before the polymerization or in situ, makes it possible to prevent the formation of trimer, which occurs during the polymerization of DMK in the presence of a Lewis acid alone. This is because the entity which initiates the polymerization produces a neutral end which thus prevents the formation of the zwitterionic intermediate to the trimer. This process thus makes it possible to operate in nonpolar solvents or solvents of moderate polarities, the toxicity of which is compatible with large scale use, in contrast to the polar solvents mentioned above, without formation of trimer.

the initiating system makes it possible to control the nature of the chain ends by choosing the nature of the initiator. Thus, a functional group which does not react in cationic polymerization but which makes possible subsequent modification of the polymer can be introduced at the chain end. Moreover, branched or star polymers can also be generated by using an initiator with a functionality of greater than 2.

the complexing agent (CoK) of the catalytic system (I+K+CoK) makes it possible, depending on its nature, to dissolve the coinitiator (K), even in a weakly polar and soluble medium, even at high concentrations of the order of 1M of Lewis acid as coinitiator (K), whereas it is generally difficult to dissolve this acid in solvents of low polarity. For example, the solubility of $AlCl_3$ in the absence of complexing agent does not exceed $1.5 \times 10^{-3}$ M in dichloromethane. Furthermore, the initiating system according to the invention exhibits an increased activity, hence the possibility of using a reduced amount of the initiating system. An increase in the kinetics of the reaction with the release of the active center (oxocarbenium) from its counteranion and the presence of a homogeneous initiating system is thus observed. A reduction in the transfer reactions by virtue of the capture of said counteranion is also observed. Chains with higher molar masses and an increase in the yield are thus obtained.

Another advantage of the washing and absorption stages is the avoidance of the presence of traces of protons (IBA) which might initiate side reactions (terminations, proton initiation, and the like).

As regards the initiator (I), it is chosen from conventional initiators participating in the composition of Friedel-Crafts systems for the cationic polymerization of olefins. It can be:

(I1) monofunctional, that is to say can exhibit a single chemical functional group and can have a following general chemical formula: $R_1$—CO—X, $R_1$—COO—$R_2$ and $R_1$—O—$R_2$, with the $R_1$ and $R_2$ groups taken from the group consisting of the following components: a hydrogen atom or an alkyl/aryl group, such as $CH_3$, $CH_3CH_2$, $(CH_3)_2CH$, $(CH_3)_3C$, $C_6H_5$ and substituted aromatic rings, it being possible for the $R_1$ and $R_2$ groups to be identical or different, and X equal to a halogen atom (F, Cl, Br or I);

(I2) difunctional, that is to say can exhibit two chemical functional groups and can have the following general chemical formula: $X_1$—CO—R—CO—$X_2$, $R_1$—O—CO—R—CO—O—$R_2$, with the R group taken from the group consisting of the following components: an alkyl/aryl group, such as $CH_3$, $CH_3CH_2$, $(CH_3)_2CH$, $(CH_3)_3C$, $C_6H_5$ and substituted aromatic rings, and the $R_1$ and $R_2$ groups taken from the group consisting of the following components: a hydrogen atom or an alkyl or aryl group, such as $CH_3$, $CH_3CH_2$, $(CH_3)_2CH$, $(CH_3)_3C$, $C_6H_5$ and substituted aromatic rings, it being possible for the $R_1$ and $R_2$ groups to be identical or different, and $X_1$ and $X_2$ taken from the group consisting of F, Cl, Br and I, it being possible for the $X_1$ and $X_2$ groups to be identical or different;

(I3) a halogenated derivative with the following general chemical formula:

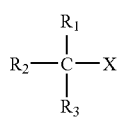

$I_{3A}$ in which X is a halogen (F, Cl, Br or I), $R_1$ is selected from the group consisting of alkyl groups of 1 to 8 carbon atoms and alkenyl groups having from 2 to 8 carbon atoms, $R_2$ is selected from the group consisting of alkyl groups having from 4 to 200 carbon atoms, alkenyl, phenyl, phenylalkyl (radical in the alkyl position) or alkylphenyl (radical in the phenyl position) groups having from 2 to 8 carbon atoms or cycloalkyl groups having from 3 to 10 carbon atoms, and $R_3$ is taken from the group consisting of alkyl groups having from 1 to 8 carbon atoms and alkenyl and phenylalkyl (alkyl radical) groups having from 2 to 8 carbon atoms; $R_1$, $R_2$ and $R_3$ can also be in the adamantyl or bornyl form with X being in a tertiary carbon position; or of following general chemical formula:

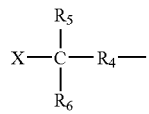

$I_{3B}$ in which X is halogen (F, Cl, Br or I), $R_5$ is taken from the group consisting of alkyl groups having from 1 to 8 carbon atoms and alkenyl groups having from 2 to 8 carbon atoms, $R_6$ is taken from the group consisting of alkyl groups having from 1 to 8 carbon atoms and alkenyl or phenylalkyl (alkyl radical) groups having from 2 to 8 carbon atoms, and $R_4$ is taken from the group consisting of the phenylene, biphenylene, $\alpha,\omega$-diphenylalkylene and —$(CH_2)_n$— groups with n an integer from 1 to 10; or of following general chemical formula:

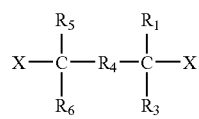

$I_{3C}$ with X, $R_1$, $R_3$, $R_4$, $R_5$ and $R_6$ as defined above;

(I4) a protic acid or Bronsted acid, such as, for example, $CF_3SO_3H$, $H_2SO_4$ or $HClO_4$, HBr, HCl and HI.

Mention may be made, by way of examples, as initiators (I), of cumyl esters of hydrocarbon acids, such as 2-acetyl-2-phenylpropane, alkyl cumyl ethers, such as 2-methoxy-2-phenylpropane or 1,4-di(2-methoxy-2-propyl)benzene, cumyl halides, particularly the chlorinated derivatives, such as 2-chloro-2-phenylpropane, (1-chloro-1-methylethyl)benzene, 1,4-di(2-chloro-2-propyl)benzene or 1,3,5-tri(2-chloro-2-propyl)benzene, aliphatic halides, particularly chlorinated derivatives, such as 2-chloro-2,4,4-trimethylpentane (TMPCl), 2-bromo-2,4,4-trimethylpentane (TMPBr) or 2,6-dichloro-2,4,4,6-tetramethylheptane, hydroxyaliphatic or hydroxycumyl compounds, such as 1,4-di(2-hydroxy-2-propyl)benzene or 2,6-dihydroxy-2,4,4,6-tetramethylheptane, 1-chloroadamantane, 1-chlorobornane, 5-(tert-butyl)-1,3-di(1-chloro-1-methylethyl)benzene and other similar compounds.

A regards the coinitiator (K), this is a Lewis acid, preferably a strong Lewis acid (such as, for example: $AlCl_3$, $AlBr_3$, $EtAlCl_2$, $BF_3$, $BCl_3$, $SbF_5$ or $SiCl_4$), in order to favor the ketone structure, of general chemical formula $R_nMX_{3-n}$, $MX_4$ or $MX_y$, depending on the nature of the element M, with:

M an element belonging to Groups IB, IIB and A, IIIB and IIIA, IVB and IVa, VB and VA, and VIIIB of the Periodic Table of the Elements; mention may be made, by way of examples, for M, of the following elements: B, Ti, Sn, Al, Hf, Zn, Be, Sb, Ga, In, Zr, V, As or Bi. Preferably, M belongs to Groups:

IIIA (formula $R_nMX_{3-n}$);

VA and VB (formula $MX_y$);

IVA and IVB (formula $MX_4$);

R a monovalent radical taken from the group consisting of hydrocarbon groups of 1 to 12 carbon atoms of alkyl, aryl, arylalkyl, alkylaryl or cycloalkyl type and alkoxys, such as, for example, the following groups: $CH_3$, $CH_3CH_2$, $(CH_3)_2CH$, $(CH_3)_3C$, $C_6H_5$, substituted aromatic rings, $OCH_3$, $OC_2H_5$ or $OC_3H_7$. The terms "arylalkyl" and "alkylaryl" refer to a radical comprising coupled aliphatic and aromatic structures, the radical being in the alkyl position in the first case and the aryl position in the second case.

X a halogen taken from the group consisting of F, Cl, Br and I, preferably Cl;

n an integer from 0 to 3 and y an integer from 3 to 5.

Mention may be made, by way of examples, of $TiCl_4$, $ZrCl_4$, $SnCl_4$, $VCl_4$, $SbF_5$, $AlCl_3$, $AlBr_3$, $BF_3$, $BCl_3$, $FeCl_3$, $EtAlCl_2$ (abbreviated to EADC), $Et_{1.5}AlCl_{1.5}$ (abbreviated to EASC) and $Et_2AlCl$ (abbreviated to DEAC), $AlMe_3$ and $AlEt_3$. The Lewis acids can also be supported on clays, zeolites, silica or silica/alumina, this making possible the recovery of the supported initiating system at the end of the reaction and thus the recycling thereof.

The Lewis acids which are particularly preferred for a cationic polymerization system are $AlCl_3$, $AlBr_3$, EADC, EASC, DEAC, $BF_3$ and $TiCl_4$.

As regards the complexing agent (CoK), this is an agent which releases the polymerization active center from the counteranion generated by the reaction between the coinitiator (K) and the initiator (I). The polymerization active center is thus rendered more accessible by virtue of the action of the CoK. The complexing agent is in particular a complexing agent which is used to complex the counteranion generated by the reaction between the coinitiator and the initiator, which has the effect of releasing the polymerization active center. Mention may be made, by way of examples, of o-chloranil (3,4,5,6,-tetrachloro-1,2-benzoquinone), p-chloranil (2,3,5, 6-tetrachloro-1,4-benzoquinone), nitrobenzene, trinitrobenzene, difluoronitrobenzene, tetracyanoethylene, pentafluorobenzene, hexafluorobenzene or octafluorotoluene.

It would not be departing from the invention if use were made of a transfer agent and/or of a chain-limiting agent well known to a person skilled in the art in the field of cationic polymerization, in addition to the main constituents of the initiating system which are cited above.

EXAMPLES

Examples of preparations of the DMK according to the invention will now be given.

The IBAN is pyrolyzed by simple thermal activation of the anhydride in a vacuum tube according to the following equation:

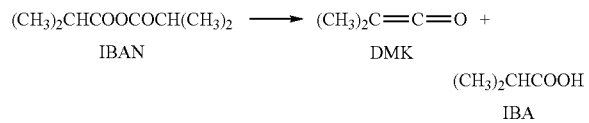

(CH$_3$)$_2$CHCOOCOCH(CH$_3$)$_2$ ⟶ (CH$_3$)$_2$C═C═O +
         IBAN                             DMK (CH$_3$)$_2$CHCOOH
IBA

In the laboratory tests, the IBAN is introduced into the reactor diluted in an inert gas (He). The tests are carried out at atmospheric pressure. The reactor is composed of two heating regions (preheating of the reactant to between 300 and 340° C. and cracking region between 400 and 500° C.). The results obtained in the laboratory are recorded in table 1 below.

| | | | | | | |
|---|---|---|---|---|---|---|
| Oven region 1 | 300° C. | 300° C. | 300° C. | 340° C. | 340° C. | 340° C. |
| Oven region 2 | 416° C. | 422° C. | 404° C. | 438° C. | 432° C. | 484° C. |
| Contact time | 0.22 s | 0.22 s | 0.21 s | 0.21 s | 0.19 s | 0.19 s |
| [IBAN] | 8% | 8% | 14% | 14% | 21% | 15% |
| Conversion | 81% | 83% | 50% | 84% | 83% | 91% |
| Cracking Sel. | 100% | 100% | 100% | 100% | 100% | 100% |
| C balance | 103% | 101% | 101% | 102% | 99% | 102% |

Oven region 1: temperature in ° C. of the preheating region of the plant.
Oven region 2: temperature in ° C. of the cracking region of the plant.
Contact time: contact time in seconds of the gas phase in the reaction region.
[IBAN]: concentration of IBAN introduced, diluted in the inert gas (He), in mol %.
Conversion: Degree of conversion = (amount in moles of IBAN converted)/(amount in moles of IBAN entering the reactor) × 100.
Cracking Sel.: cracking selectivity = (number of moles of DMK obtained)/(number of moles of IBAN converted) × 100.
C balance: degree of cracking = (number of moles of DMK, of IBA and of IBAN exiting from the reactor)/(number of moles of IBAN entering the reactor) × 100.

What is claimed is:

1. A process for the preparation of dimethylketene (DMK) by pyrolysis of isobutyric anhydride (IBAN), in which:
   a) a mixture comprising 1 to 50% by volume of IBAN and 99 to 50% of inert gas is preheated at atmospheric pressure between 300 and 340° C.,
   b) this mixture is then brought to a temperature of between 400 and 550° C. for a contact time of between 0.05 and 10 s, in order to obtain a mixture of DMK, of inert gas, of isobutyric acid (IBA) and of unreacted IBAN,
   c) the mixture resulting from b) is cooled in a condensation stage, in order to separate the gas mixture comprising the DMK from the condensed IBA and/or condensed IBAN.

2. The process as claimed in claim 1, in which the inert gas is chosen from nitrogen and helium.

3. The process as claimed in claim 1, in which the proportions of IBAN and of inert gas are from 5 to 50% by volume of IBAN and 95 to 50% of inert gas.

4. The process as claimed in claim 1, in which the proportions of IBAN and of inert gas are from 8 to 21% by volume of IBAN and 92 to 79% of inert gas.

5. The process as claimed in claim 1, in which the contact time is between 0.15 and 0.25 seconds.

6. The process as claimed in claim 1, in which the gas mixture comprising DMK and resulting from stage c) is brought into contact with a washing solution in order to reduce, the traces of IBA and/or of IBAN included in said gas mixture and to obtain the DMK with a purity sufficient to polymerize it.

7. The process as claimed in claim 6, characterized in that the gas mixture comprising the DMK resulting from stage c) is washed in a washing column equipped with a demister.

8. The process as claimed in claim 7, characterized in that the demister is situated either at the column top or at the column bottom.

9. The process as claimed in claim 7, characterized in that the gas mixture enters at the bottom of the washing column, whereas the washing solvent enters at the column top.

10. The process as claimed claim 6, in which the washing solution is IBAN or a saturated or unsaturated, aliphatic or alicyclic, substituted or unsubstituted hydrocarbon.

11. The process as claimed in claim 1, in which:
   d) the gas mixture comprising the DMK is absorbed in a solvent of saturated or unsaturated, aliphatic or alicyclic and substituted or unsubstituted hydrocarbon type, and
   e) polymerization is then carried out, in said solvent comprising the DMK, to give PDMK in the presence of a cationic initiating system comprising an initiator (I), a coinitiator (K) and a complexing agent (CoK), and
   f) at the end of the polymerization, the unreacted DMK is removed and the PDMK is separated from the solvent and from the residues of the cationic initiating system.

12. The process as claimed in claim 11, in which the complexing agent (CoK) is an agent which releases the polymerization active center from its counteranion generated by the reaction between the coinitiator (K) and the initiator (I).

13. The process as claimed in claim 12, characterized in that the complexing agent (CoK) is a molecule having at least one double bond depleted in electrons by an electron-withdrawing group.

14. The process as claimed in claim 13, in which the complexing agent (CoK) is selected from the group: o-chloranil (3,4,5,6,-tetrachloro-1,2-benzoquinone), p-chloranil (2,3,5,6-tetrachloro-1,4-benzoquinone), nitrobenzene, trinitrobenzene, difluoronitrobenzene, tetracyanoethylene, pentafluorobenzene, hexafluorobenzene and octafluorotoluene.

15. The process as claimed in claim 11, in which the coinitiator (K) comprises an element (M) belonging to Groups IB, IIB and A, IIIB and IIIA, IVB and IVA, VB and VA, and VIIIB of the Periodic Table of the Elements.

16. The process as claimed in claim 15, characterized in that the element (M) is taken from the group consisting of the chemical elements B, Ti, Sn, Al, Hf, Zn, Be, Sb, Ga, In, Zr, V, As and Bi.

17. The process as claimed in claim 15, in which the coinitiator (K) is a Lewis acid of general formula $R_nMX_{3-n}$ where M is an element belonging to Group IIIA, coinitiator (K) is of general formula $MX_4$ where M is an element belonging to Groups VA, IVA and IVB and coinitiator (K) is of general formula $MX_5$ where M is an element belonging to Group VB, with:

- R a monovalent radical taken from the group consisting of the hydrocarbon groups of 1 to 12 carbon atoms of alkyl, aryl, arylalkyl, alkylaryl or cycloalkyl type and alkoxys;
- X a halogen atom taken from the group consisting of F, Cl, Br and I;
- n an integer from 0 to 3.

18. The process as claimed in claim 15, in which the coinitiator (K) is taken from the group consisting of $TiCl_4$, $ZrCl_4$, $SnCl_4$, $VCl_4$, $SbF_5$, $AlCl_3$, $AlBr_3$, $BF_3$, $BCl_3$, $FeCl_3$, $EtAlCl_2$, $Et_{1.5}AlCl_{1.5}$, $Et_2AlCl$, $AlMe_3$ and $AlEt_3$.

19. The process as claimed in claim 11, in which the initiator (I) is selected from the group consisting of monofunctional molecules (I1), difunctional molecules (I2), molecules substituted by one or more halogen atoms (I3)Brönsted acids (I4).

20. The process as claimed in claim 7, characterized in that the demister is situated at the column top.

\* \* \* \* \*